(12) United States Patent
Doherty (10) Patent No.: US 6,547,394 B2
(45) Date of Patent: Apr. 15, 2003

(54) HAND-HELD OPHTHALMIC ILLUMINATOR

(76) Inventor: Victor J. Doherty, 32 Sterling Rd., Wellesley, MA (US) 02482

(*) Notice: Subject to any disclaimer, the term of this patent is extended or adjusted under 35 U.S.C. 154(b) by 0 days.

(21) Appl. No.: 09/768,731

(22) Filed: Jan. 24, 2001

(65) Prior Publication Data

US 2001/0038439 A1 Nov. 8, 2001

Related U.S. Application Data

(63) Continuation-in-part of application No. 09/175,796, filed on Oct. 20, 1998, now abandoned.

(51) Int. Cl.⁷ .................................................. A61B 3/10
(52) U.S. Cl. ...................................................... 351/221
(58) Field of Search ................................ 351/205, 206, 351/221; 315/362; 600/321, 431, 558

(56) References Cited

U.S. PATENT DOCUMENTS

| 3,945,717 A | 3/1976 | Ryder et al. |
| 4,964,023 A | 10/1990 | Nishizawa et al. |
| 6,340,868 B1 * | 1/2002 | Lys et al. .................... 315/362 |
| 2001/0007494 A1 | 7/2001 | Takada |

FOREIGN PATENT DOCUMENTS

JP 2000-1314 A1 7/2001

* cited by examiner

Primary Examiner—George Manuel (57) ABSTRACT

The invention provides an ophthalmic illuminator, including a battery, an electrical resistor, an electrical switch and an LED. The battery is in circuit with the battery; and the electrical switch is in circuit with the resistor, where electrical energy flows through the circuit when the switch is in the closed position. The light emitting diode is in circuit with the switch and generates blue light energy which in turn causes fluorescence in a fluorescien dye administered to the patient's eye when the switch is in the closed position. An optical element (e.g, a lens or reflector) can be disposed between the diode and the eye to increase blue light energy reaching the eye. The energy can be "pulsed" such that the diode generates the blue light at a predetermined frequency. A user of the illuminator, e.g., a physician, can hold the system by hand to operate the switch (e.g., through a button). A magnifier coupled to the system provides a magnified image of the patient's eye, if desired. Preferably, an annular housing integrates the LED (or a plurality of LEDs) together such that a button activates and generates the blue light energy, and a user views through the center of the housing, through a magnifier therein, to view the patient's eye.

20 Claims, 6 Drawing Sheets

HAND-HELD OPHTHALMIC ILLUMINATOR

RELATED APPLICATIONS

This application is a continuation-in-part of, and claims priority to, commonly owned U.S. application Ser. No. 09/175,796, filed on Oct. 20, 1998 now abandoned and hereby incorporated by reference.

BACKGROUND OF THE INVENTION

Ophthalmologists, optometrists and other medical doctors and health care professionals frequently are required to examine the cornea of the human eye for scrapes, abrasions, dirt or foreign bodies. The current technology utilizes a battery operated hand-held penlight illuminator in conjunction with a solution of Sodium Fluorescein. An example of an existing prior art device is the Solan Blu-Slit® manufactured by Xomed Surgical Products, Inc. of Jacksonville, Fla. The penlight illuminator typically uses conventional batteries as a power source and an incandescent or halogen light bulb. A cobalt blue filter attached over the lamp filters the white light emitted by the bulb to produce a blue beam. This blue beam is used to illuminate the patient's eye after application of the Sodium Fluorescein dye.

The fluorescein dye, which is typically impregnated in sterile paper, is administered by the physician in the following manner. The patient's upper eyelid is retracted and the sodium fluorescein impregnated paper applicator is made to contact the bulbar conjunctiva of the eye at the temporal side. The applicator is removed and the eyelid is opened and closed several times to allow diffusion of the dye over the entire conjunctival area and cornea.

The fluorescein dye tends to accumulate in epithelial defects of the cornea and illumination of the eye will cause the defect to fluoresce vividly. By using blue filtered light to illuminate the eye of the patient, which has been dyed with fluorescein, this fluorescence is most observable. The amount of fluorescence observable is proportional to the accumulation of the fluorescein or the magnitude of the defect. However, the magnitude of the fluorescence is also proportional to both the intensity and spectral purity of the light illuminating the patient's eye. In other words, a brighter and more spectrally pure beam will show more detail and thus is more desirable to the physician.

SUMMARY OF THE INVENTION

The subject of this invention is a device which is used to illuminate a patient's eye that has been administered with a fluorescent dye for the purpose of examining the eye for epithelial defects. The invention in its simplest form utilizes four components: a battery, an electrical resistor, an electrical switch and a blue light emitting diode.

BRIEF DESCRIPTION OF THE INVENTION

DETAILED DESCRIPTION OF THE INVENTION

Figure 1:
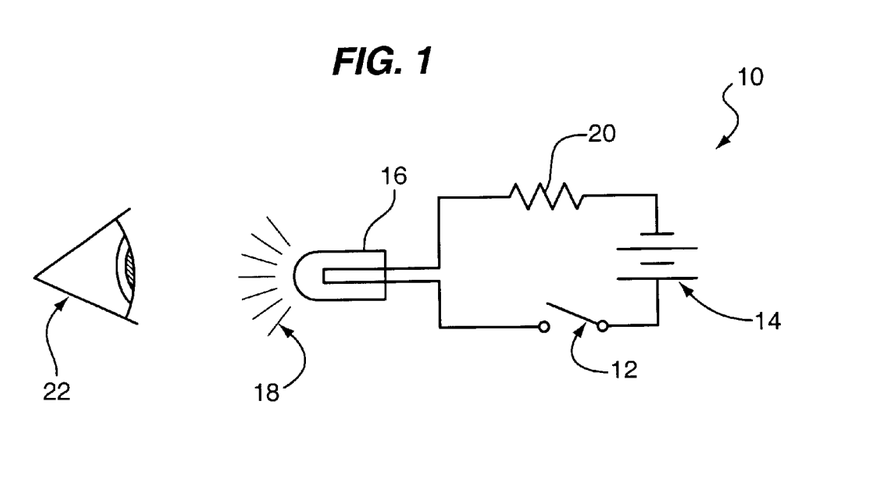
FIG. 1 depicts an electrical schematic of an ophthalmic illuminator utilizing a blue LED source, according to the invention.

In schematic 10 of FIG. 1, when the switch 12 is closed electrical energy from the battery 14 flows through the circuit 10 and causes the blue LED 16 to produce blue light 18. The resistor 20 is used to limit the current that is applied to the LED 16 as per the manufacturer specifications which is typically 20 to 30 milli-amps. Certain LED's have an internal resistor 20 built into the LED package, as known in the art. Battery 14 voltage is typically four to twelve volts DC. The blue LED's are for example manufactured by both CREE and NICHIA and typically produce illumination on the order of 0.50 candle or more at a wavelength of 450 nano-meters with a typical bandpass of 50 nm. These LED's typically are comprised of Gallium Nitride on a Silicon Carbide substrate (NICHIA) or just Silicon Carbide (CREE). In one embodiment of the invention, resistor 20 is not required; rather, battery 14 serves as the resistor for circuit 10.

The ophthalmic illuminator as depicted in FIG. 1 is superior to the current incandescent technology for the following reasons: first, the blue LED 16 emits more illumination in the desired blue spectrum (425 to 475 NM) than the filtered incandescent lamp which results in more fluorescence of the fluorescein dyed eye 22 and thus has better sensitivity; second, the blue LED 18 uses less power than a blue optically filtered incandescent or halogen bulb so that the battery power source 14 should last significantly longer; third, the invention is simpler to the prior art technology in that there is no need for a blue bandpass optical filter.

There are a number of enhancements that can be made to the basic invention as shown in FIG. 1. First, a lens 24 may be added close to the LED 18 between the LED 18 and the patient's eye 22 to maximize the light collection efficiency of the system. A reflector could be added separately or used in conjunction with a lens for the same purpose. Second, the electrical circuit 10 could be modified with a pulse means 13 to cause the blue LED 16 to operate in a pulsed mode instead of continuous mode. This would enable higher peak current to be applied to the blue LED 16 to produce the appearance of an even brighter beam and hence more fluorescence sensitivity to the physician. Third, a simple magnifier tens could be added to the device 10 to provide a magnified view of the patient's eye 22 to the physician or user (see FIG. 2). The fixed magnification of this lens would typically be chosen to between 1.5x and 15x. Typically the magnifications are between 2x and 10x. A variable focal length zoom lens could also be substituted as the simple magnifier to provide a range of magnification for the physician user.

The invention described here can be manufactured as a stand-alone hand held device or incorporated into other ophthalmic diagnostic instruments such as a table-top or hand held slit lamp.

Figure 2:
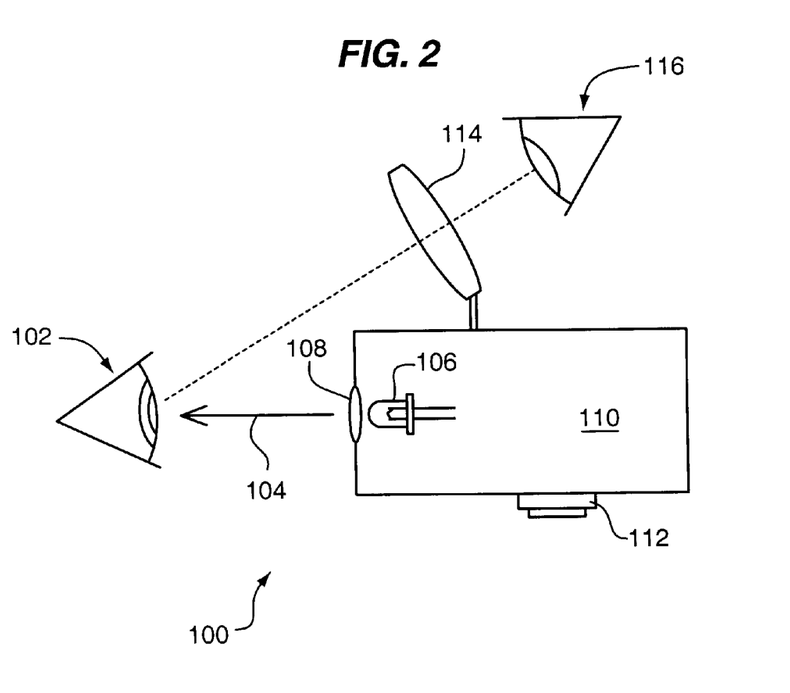
FIG. 2 shows an alternative ophthalmic illuminator of the invention.

FIG. 2 shows an alternative system 100 of an ophthalmic illuminator constructed according to the invention. FIG. 2 also shows the patient's eye 102 illuminated by blue light 104 generated by the diode 106. The light 104 is preferably coupled to the eye 102 through an optical lens (or reflector, known in the art) 108 to increase the blue light energy at the eye 102.

System 100 preferably integrates to a common housing 110 such that a user can hold the system 100 during, treatment of the eye 102. Although not shown, the circuit of FIG. 1 can reside within the housing 110; and a button 112 can be used to operate the switch 12 (FIG. 1) which in turn causes the generation of light 104. The button 112 is for example operated by a physician's finger.

System 100 can also include a magnifier 114 coupled to the housing 110 such that the physician's eye 116 can view the patient's eye 102 with increased magnifier. A zoom lens (known in the art can replace the magnifier 114 such that selective control of that magnification is achieved.

Figure 3:
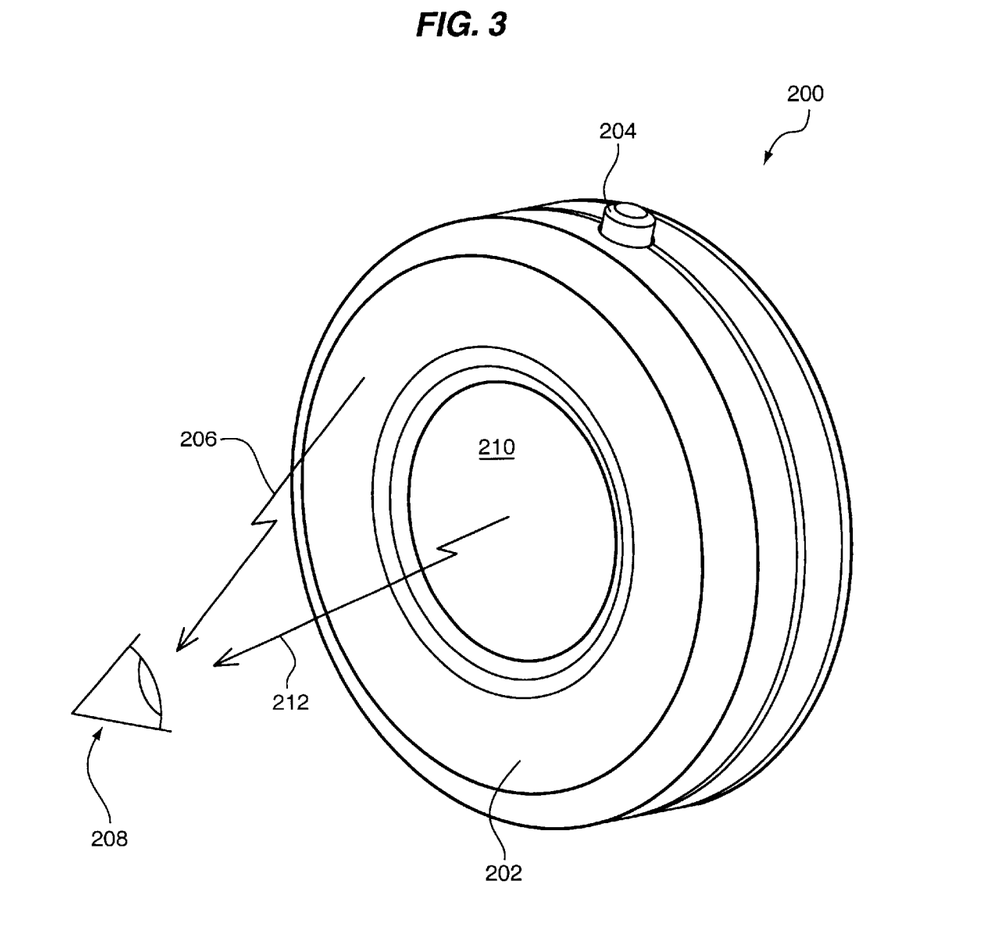
FIG. 3 shows a perspective view of a hand held eye illuminator constructed according to the invention.

FIG. 3 shows a hand held illuminator 200 constructed according to the invention. Illuminator 200 has an annular housing 202 that contains circuitry such as schematic 10 of FIG. 1. A button 204 is arranged with housing 202 such that a user may press to generate light energy 206 to illuminate a patient's eye 208. Button 204 for example functions as switch 12, FIG. 1. A user of illuminator 200 may then peer through aperture 210, along path 212, to conveniently view patient eye 208. Aperture 210 may optionally include a magnifying lens, or zoom lens, according to preferred embodiments of the invention. Sources for generating energy 206 include a LED such as LED 16, FIG. 1. Sources may be integrated with housing 202 in various ways as illustrated below. In accord with the invention, energy 206 delivered from sources (e.g., LEDs) may be considered a transmit channel while path 212 may be considered a receive channel. In one embodiment of the invention, the energy is blue light that creates green fluorescence from the eye; and thus a lens in aperture 210 is preferably coated with a green filter thin film coating to filter light along the receive channel.

Figure 4:
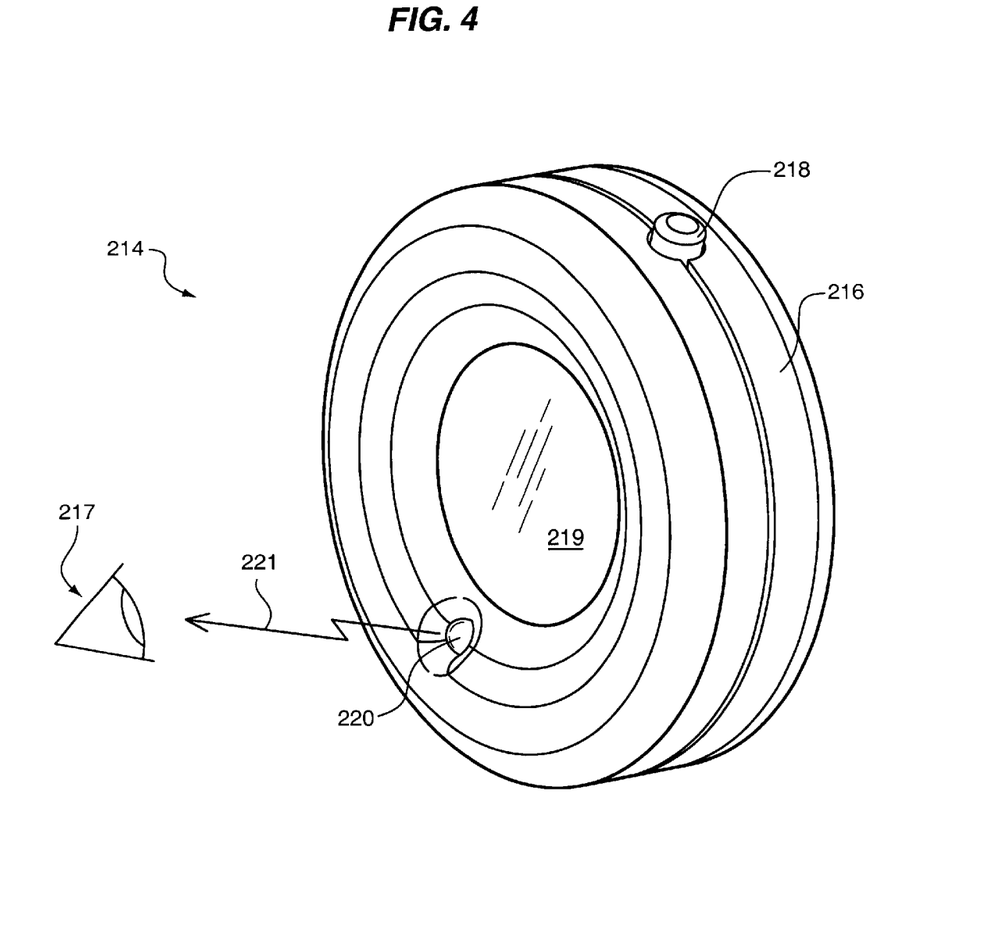
FIG. 4 shows a perspective view of another hand held eye illuminator constructed according to the invention.

FIG. 4 shows a hand held illuminator 214 constructed according to the invention. Illuminator 214 has an annular housing 216 that contains circuitry such as schematic 10 of FIG. 1. A button 218 is arranged with housing 216 such that a user may press to generate light energy 221 to illuminate a patient's eye 217, as above. Button 218 for example functions as switch 12, FIG. 1. Illuminator 214 further has an optical magnifier in the form of a lens 219 for a user to peer through to conveniently view patient eye 217. A LED 220 integrates with housing 216 to generate light energy 218. LED 220 may optionally include a focusing lens, though one is not required.

Figure 5:
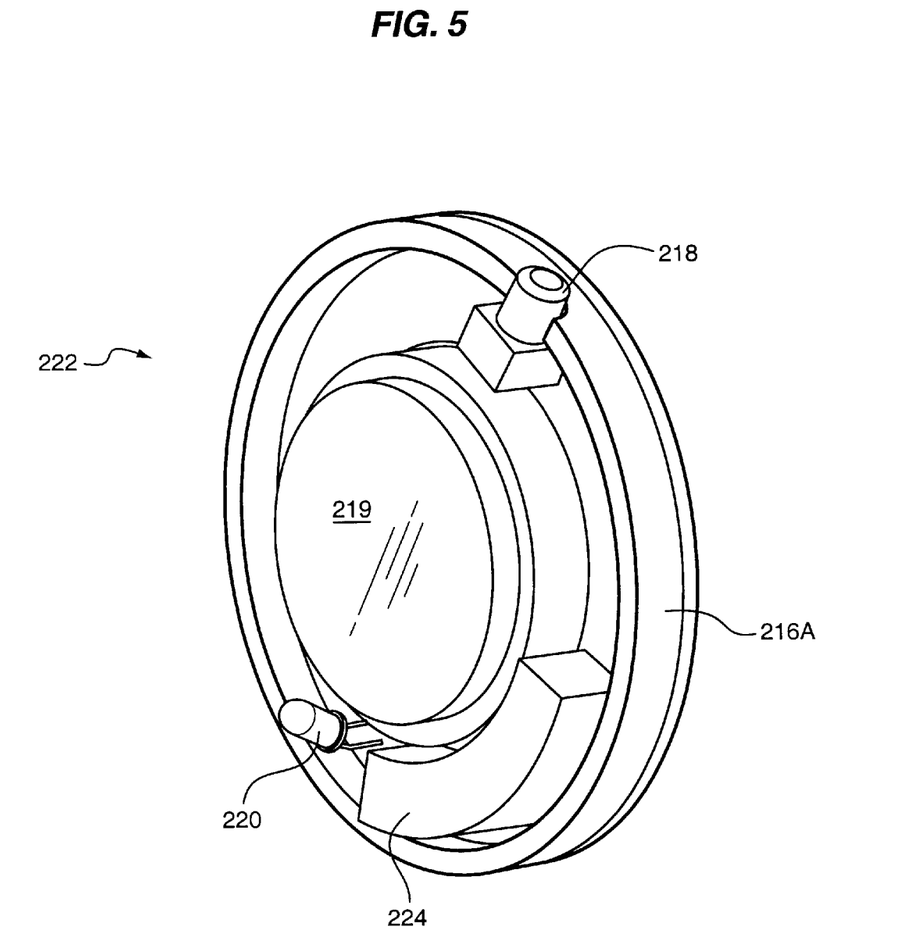
FIG. 5 shows a perspective interior view of the illuminator of FIG. 4.

FIG. 5 shows an interior portion 222 of illuminator 214. Specifically, interior portion 222 shows further features of button 218 and LED 220, each connected in circuit to internal battery 224. Battery 224 for example operates as in battery 14, FIG. 1, to power LED 220. Element 216a forms the back of housing 216.

Figure 6:
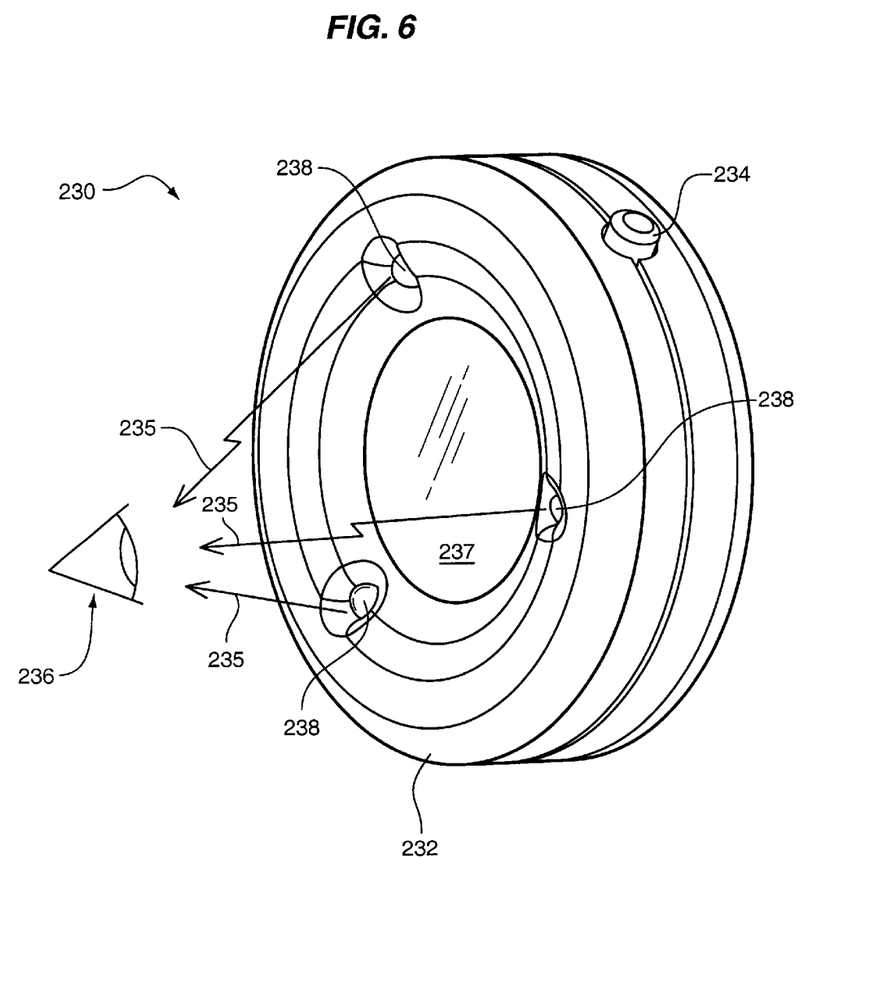
FIG. 6 shows a perspective view of another hand held eye illuminator constructed according to the invention.

FIG. 6 shows a hand held illuminator 230 constructed according to the invention. Illuminator 230 has an annular housing 232 that contains circuitry such as schematic 10 of FIG. 1. A button 234 is arranged with housing 232 such that a user may press to generate light energy 235 to illuminate a patient's eye 236. Button 234 for example functions as switch 12, FIG. 1. Though not required, illuminator 230 further has an optical magnifier in the form of a lens 237 for a user to peer through to conveniently view patient eye 236. A plurality of LEDs 238 integrate with housing 232 to generate light energy 235. Each of LEDs 238 may optionally include a focusing lens, though one is not required. Although three LEDs 238 are shown, more or fewer LEDs can be used without departing from the scope of the invention.

Figure 7:
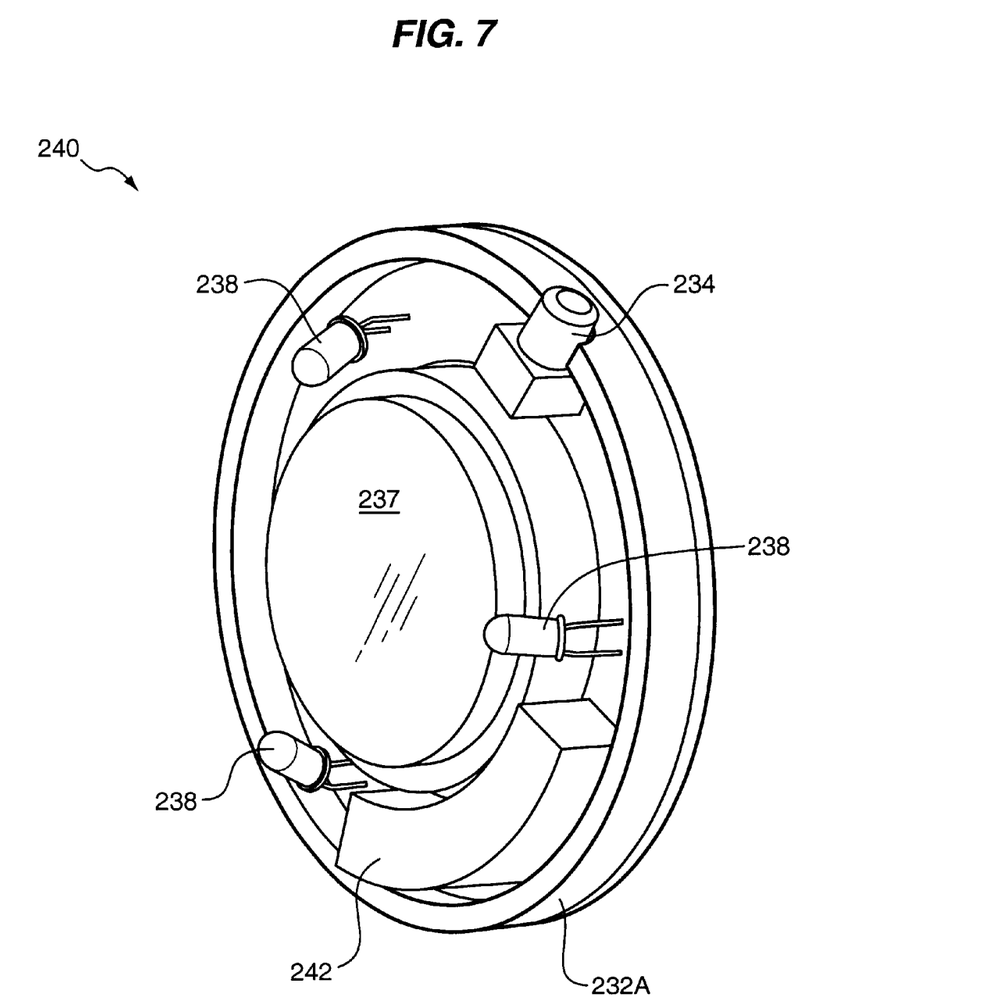
FIG. 7 shows a perspective interior view of the illuminator of FIG. 6.

FIG. 7 shows an interior portion 240 of illuminator 230. Specifically, interior portion 240 shows further features of button 234 and LEDs 238, each connected in circuit to internal battery 242. Battery 242 for example operates as in battery 14, FIG. 1, to power LEDs 238. Element 232a forms the back of housing 232.

In addition to the advantages apparent in the foregoing description, the invention may have application in other fields outside of ophthalmology. For example, in the field of dermatology, an illuminator of the invention may be used to illuminate skin, along the transmit channel, and to view the skin along the receive channel.

In view of the foregoing,

What is claimed is:

1. An ophthalmic illuminator, comprising:
   a battery;
   an electrical resistor in circuit with the battery;
   an electrical switch in circuit with the resistor;
   at least one light emitting diode, in circuit with the switch, for generating blue light energy in response to activation of the switch; and
   a fluorescein dye administered to a patent's eye, the dye being responsive to the energy to fluoresce.

2. An illuminator of claim 1, further comprising an optical element disposed between the diode and the eye to increase blue. light energy reaching the eye.

3. An illuminator of claim 2, wherein the element is one of a lens or a powered reflector.

4. An illuminator of claim 1, further comprising electronics for cyclically energizing the diode, wherein the diode generates the blue light at a predetermined frequency in order to increase the illumination appearance of the energy.

5. An illuminator of claim 1, further comprising a housing for integrating the battery, switch, resistor and diode into an integral package, the diode being positioned to generate blue light energy away from the package, and further comprising a magnifier lens coupled to the housing for providing a magnified image of the patient's eye to a user of the illuminator.

6. An illuminator of claim 5, wherein the magnifier lens has a magnification between about 1.5× and 15×.

7. An illuminator of claim 1, further comprising a housing for integrating the battery, switch, resistor and diode into an integral package, the diode being positioned to generate blue light energy away from the package, and further comprising a zoom lens coupled to the housing for providing a selective magnified image of the patient's eye to a user of the illuminator.

8. An illuminator of claim 1, wherein the dye comprises Sodium Fluorescein.

9. An illuminator of claim 1, wherein the diode comprises Gallium nitride.

10. An illuminator of claim 1, wherein the diode comprises Silicon Carbide.

11. An illuminator of claim 1, further comprising a substantially annular housing constructed and arranged with a button for operating the switch, a user of the illuminator viewing through an aperture in the housing to view the patient's eye.

12. An illuminator of claim 11, further comprising a magnifying lens constructed and arranged with the aperture, for magnifying the patient's eye for the user.

13. An illuminator of claim 11, further comprising a plurality of light emitting diodes, each diode responsive to activation by the button to generate the blue light.

14. An illuminator of claim 1, further comprising a focusing lens constructed and arranged with at least one of the diodes to focus the blue light energy onto the patient's eye.

15. A method for illuminating a patient's eye for ophthalmic examination, comprising the steps of: administering a fluorescein dye to the patent's eye, illuminating the eye with blue light energy generated from one or more light emitting diodes, the dye being responsive to the blue light energy to fluoresce, and viewing the patient's eye, and viewing the eye while the dye fluoresces.

16. A method of claim 15, wherein the step of administering a fluorescein dye comprises administering Sodium Fluorescein to the eye.

17. A method of claim 15, wherein the step of illuminating the eye comprises pressing a button on an annular-shaped housing, and wherein the step of viewing the patient's eye comprises viewing through a center of the housing.

18. A method of claim 15, wherein the step of illuminating comprises generating light from a plurality of light emitting diodes.

19. A method of claim 15, wherein the step of viewing comprises viewing through a magnifying lens coupled with a housing that supports the diodes.

20. A method of claim 15, further comprising the step of focusing the blue light energy onto the patient's eye.

* * * * *

(12) INTER PARTES REVIEW CERTIFICATE (2249th)
United States Patent
Doherty (10) Number: US 6,547,394 K1
(45) Certificate Issued: Aug. 17, 2021

(54) HAND-HELD OPTHALMIC ILLUMINATOR (75) Inventor: Victor J. Doherty (73) Assignee: EIDOLON OPTICAL, LLC

Trial Number:

IPR2018-01311 filed Jun. 25, 2018

Inter Partes Review Certificate for:

Patent No.: 6,547,394
Issued: Apr. 15, 2003
Appl. No.: 09/768,731
Filed: Jan. 24, 2001

The results of IPR2018-01311 are reflected in this inter partes review certificate under 35 U.S.C. 318(b).

INTER PARTES REVIEW CERTIFICATE
U.S. Patent 6,547,394 K1
Trial No. IPR2018-01311
Certificate Issued Aug. 17, 2021

AS A RESULT OF THE INTER PARTES REVIEW PROCEEDING, IT HAS BEEN DETERMINED THAT:

Claims 1, 5, 6, 8-10, 14-16 and 19 are found patentable.

\* \* \* \* \*